(12) United States Patent
Vollmann et al.

(10) Patent No.: US 9,701,572 B2
(45) Date of Patent: Jul. 11, 2017

(54) METHOD FOR PRODUCING A LITHIUM SILICATE GLASS BLANK AND A LITHIUM SILICATE GLASS-CERAMIC BLANK

(71) Applicant: DENTSPLY International Inc., York, PA (US)

(72) Inventors: Markus Vollmann, Gelnhausen (DE); Udo Schusser, Alzenau (DE)

(73) Assignee: DENTSPLY INTERNATIONAL INC., York, PA (US)

( * ) Notice: Subject to any disclaimer, the term of this patent is extended or adjusted under 35 U.S.C. 154(b) by 0 days.

(21) Appl. No.: 14/671,253

(22) Filed: Mar. 27, 2015

(65) Prior Publication Data

US 2015/0274580 A1   Oct. 1, 2015

(30) Foreign Application Priority Data

Mar. 28, 2014   (DE) ........................ 10 2014 104 401

(51) Int. Cl.
| | | |
|---|---|---|
| C03C 10/00 | (2006.01) | |
| A61C 13/00 | (2006.01) | |
| C03B 19/02 | (2006.01) | |
| A61K 6/02 | (2006.01) | |
| A61K 6/027 | (2006.01) | |
| C03C 3/097 | (2006.01) | |
| C03C 4/00 | (2006.01) | |
| C03B 32/02 | (2006.01) | |

(52) U.S. Cl.
CPC ...... C03C 10/0009 (2013.01); A61C 13/0022 (2013.01); A61K 6/024 (2013.01); A61K 6/0273 (2013.01); C03B 19/02 (2013.01); C03B 32/02 (2013.01); C03C 3/097 (2013.01); C03C 4/0021 (2013.01); C03C 10/0027 (2013.01)

(58) Field of Classification Search
CPC .......... C03C 10/00; C03B 19/02; A61C 13/00
USPC ............................. 65/136.4; 428/432; 264/19
See application file for complete search history.

(56) References Cited

U.S. PATENT DOCUMENTS

| | | | | |
|---|---|---|---|---|
| 6,048,589 A | * | 4/2000 | Suzuki ................ | C03C 10/0027 427/129 |
| 6,402,288 B2 | * | 6/2002 | Rhodes ................ | B41J 2/16511 347/29 |
| 9,314,408 B2 | * | 4/2016 | Blomker .............. | A61K 6/0047 |
| 2011/0256409 A1 | * | 10/2011 | Ritzberger ........... | A61K 6/0215 428/432 |
| 2011/0257000 A1 | * | 10/2011 | Ritzberger ........... | A61K 6/0215 501/32 |
| 2012/0248642 A1 | * | 10/2012 | Ritzberger ........... | A61K 6/0215 264/19 |
| 2012/0309607 A1 | * | 12/2012 | Durschang ............ | A61K 6/024 501/59 |
| 2013/0323404 A1 | * | 12/2013 | Ritzberger ........... | A61K 6/0215 427/2.29 |
| 2014/0000314 A1 | * | 1/2014 | Ritzberger ........... | A61K 6/0215 65/33.1 |
| 2014/0200129 A1 | * | 7/2014 | Durschang ............ | C03B 32/02 501/32 |
| 2014/0335473 A1 | * | 11/2014 | Ritzberger ........... | A61K 6/0215 433/215 |

FOREIGN PATENT DOCUMENTS

EP   2623087   *   2/2013

* cited by examiner

*Primary Examiner* — Mark Halpern
(74) *Attorney, Agent, or Firm* — Leana Levin; Douglas J. Hura; David A. Zdurne

(57) ABSTRACT

The invention relates to a method for producing a blank of lithium silicate glass a starting composition of at least 8 wt-% of a stabilizer selected from the group consisting of $ZrO_2$, $HfO_2$, and mixtures thereof, wherein the method includes the steps of mixing the raw materials comprising the stabilizer in powder form, wherein the powder of the stabilizer has a particle size $d_{50}=x$ with 0.3 µm≤x≤1.5 µm, melting the raw materials in a crucible at a temperature $T_{AU}$ and storing the melt in the crucible for a time $t_H$, pouring the homogenized melt into molds, wherein the melt flows out of the crucible with a discharge temperature $T_{AB}$ being $T_{AU} \geq T_{AB}$, wherein the filling of the molds and the molding of the melt in the molds takes place with a cooling rate A.

29 Claims, No Drawings

METHOD FOR PRODUCING A LITHIUM SILICATE GLASS BLANK AND A LITHIUM SILICATE GLASS-CERAMIC BLANK

RELATED APPLICATIONS

This patent application claims the benefit of and priority to German Patent Application Ser. No. DE 102014104401.0, filed on Mar. 28, 2014, which is herein incorporated by reference for all purposes.

FIELD OF INVENTION

The invention relates to a method for producing a lithium silicate glass blank with a composition of at least 8 wt-%, preferably 9 to 20 wt-%, of a stabilizer selected from the group $ZrO_2$, $HfO_2$, or mixtures thereof. The invention also relates to a method for producing a lithium silicate glass-ceramic blank, and the use of the lithium silicate glass-ceramic blank. The invention also relates to the use of the lithium silicate glass-ceramic blank as well as to a dental product.

BACKGROUND OF THE INVENTION

Lithium silicate glass-ceramic blanks have been proven their value in the field of dental prosthetics due to their strength and biocompatibility. There is the advantage that, if a lithium silicate blank comprises lithium metasilicate as main crystalline phase, an easy machining is possible without undue wear of tools. If then a heat treatment takes place, during which the product is converted into a lithium disilicate glass-ceramic, a high strength is obtained. Also good optical properties and a good chemical stability are given. Respective methods are disclosed in DE 197 50 794 A1, or DE 103 36 913 B4.

It has been shown that the strength is increased and a good translucence can be reached, if at least a stabilizer selected from the group zirconium oxide, hafnium oxide, or mixtures thereof, especially zirconium oxide, is added to the starting raw materials in form of lithium carbonate, quartz, aluminum oxide, etc., which are usual initial components. The percentage by weight of the stabilizer in the initial composition can be as high as 20%. In this respect, reference is made to DE 10 2009 060 274 A1, or WO 2012/175450 A1, WO 2012/175615 A1, WO 2013/053865 A2, or EP 2 662 342 A1.

In practice, however, problems arise in such a way that after the final crystallization, i.e., especially at the stage when lithium disilicate is existent as main crystalline phase in the lithium silicate glass, the stabilizers, especially zirconium oxide, recrystallize although the latter had been fully dissolved in the glass phase of the lithium silicate before.

SUMMARY OF INVENTION

The present invention seeks to improve upon prior lithium silicate glass materials by providing improved lithium silicate glass materials, products, and methods for forming thereof. In one aspect, the present invention provides a method for producing a lithium silicate glass blank with a composition of at least 8 wt-%, preferably 9 to 20 wt-%, of a stabilizer selected from the group $ZrO_2$, $HfO_2$, or mixtures thereof, comprising the method steps of: mixing the raw materials comprising the stabilizer in powder form, wherein the powder of the stabilizer has a particle size $d_{50}=x$ with 0.3 µm≤x≤1.5 µm, melting the raw materials in a crucible at a temperature $T_{AU}$ and storing the melt in the crucible for a time $t_H$, and pouring the homogenized melt into molds, wherein the melt flows out of the crucible with a discharge temperature $T_{AB}$ being $T_{AU} \geq T_{AB}$, wherein the filling of the molds and the molding of the melt in the molds takes place with a cooling rate A.

In another aspect, the present invention contemplates a method for producing a lithium silicate glass blank with a composition of at least 8 wt-%, preferably 9 to 20 wt-%, of a stabilizer selected from the group $ZrO_2$, $HfO_2$, or mixtures thereof, comprising the method steps of: mixing the raw materials comprising the stabilizer in powder form, wherein the powder of the stabilizer has a particle size $d_{50}=x$ with 0.3 µm≤x≤1.5 µm, melting the raw materials in a crucible at a temperature $T_{AU}$ and storing the melt in the crucible for a time $t_H$, and pouring the homogenized melt into molds, wherein the melt flows out of the crucible with a discharge temperature $T_{AB}$ being $T_{AU} - Y° C. = T_{AB}$ with 150° C.≤Y≤350° C. and $T_{AU} \geq 1400°$ C., wherein the filling of the molds and the shaping of the melt in the molds takes place with a cooling rate A.

In another aspect, the present invention contemplates a method for producing a lithium silicate glass blank with a composition of at least 8 wt-%, preferably 9 to 20 wt-%, of a stabilizer selected from the group $ZrO_2$, $HfO_2$, or mixtures thereof, comprising the method steps of: mixing the raw materials comprising the stabilizer in powder form, wherein the powder of the stabilizer has a particle size $d_{50}=x$ with 0.3 µm≤x≤1.5 µm, melting the raw materials in a crucible at a temperature $T_{AU}$ and storing the melt in the crucible for a time $t_H$, and pouring the homogenized melt into molds, wherein the melt flows out of the crucible with a discharge temperature $T_{AB}$ being $T_{AU} \geq T_{AB}$, wherein the filling of the molds and the molding of the melt in the molds takes place with a cooling rate A with 5 K/sec≤A≤100 K/sec up to a temperature $T_M$ with $T_M \geq 600°$ C., particularly 600° C.≤$T_M$≤650° C.

In another aspect, the present invention contemplates a method for producing a lithium silicate glass blank with a composition of at least 8 wt-%, preferably 9 to 20 wt-%, of a stabilizer selected from the group $ZrO_2$, $HfO_2$, or mixtures thereof, comprising the method steps of: mixing the raw materials comprising the stabilizer in powder form, wherein the powder of the stabilizer has a particle size $d_{50}=x$ with 0.3 µm≤x≤1.5 µm, melting the raw materials in a crucible at a temperature $T_{AU}$ with 1450° C.≤$T_{AU}$≤1600° C. and storing the melt in the crucible for a time $t_H$ with $t_H \geq 1$ h, and pouring the homogenized melt into molds, wherein the melt flows out of the crucible with a discharge temperature $T_{AB}$ being $T_{AU} \geq T_{AB}$, wherein the filling of the molds and the molding of the melt in the molds takes place with a cooling rate A.

In another aspect, the present invention contemplates a method for producing lithium silicate glass blank with a composition of at least 8 wt-%, preferably 9 to 20 wt-%, of a stabilizer selected from the group $ZrO_2$, $HfO_2$, or mixtures thereof, comprising the method steps of: mixing the raw materials comprising the stabilizer in powder form, wherein the powder of the stabilizer has a particle size $d_{50}=x$ with 0.3 µm≤x≤1.5 µm, melting the raw materials in a crucible at a temperature $T_{AU}$ with 1450° C.≤$T_{AU}$≤1600° C. and storing the melt in the crucible for a time $t_H$ with $t_H \geq 1$ h, and pouring the homogenized melt into molds, wherein the melt flows out of the crucible with a discharge temperature $T_{AB}$ being $T_{AU} - Y° C. = T_{AB}$ with 150° C.≤Y≤350° C. and $T_{AU} \geq 1400°$ C., wherein the filling of the molds and the molding of the melt in the molds takes place with a cooling rate A with ≤K/sec≤A≤100 K/sec up to a temperature $T_M$ with 600° C.≥$T_M$, particularly 600° C.≤$T_M$≤650° C.

In another aspect, the present invention contemplates a use of the lithium silicate glass-ceramic blank according to any of the methods discussed herein as dental material, or as component of a dental material.

In another aspect, the present invention contemplates a dental product made of a lithium silicate glass-ceramic blank according to any of the methods described herein.

In yet another aspect, any of the aspects of the present invention may be further characterized by one or any combination of the following features: wherein the melt flows out of the crucible with a discharge temperature $T_{AB}$ with $T_{AU}$-Y° C.=$T_{AB}$ with 150° C.≤Y≤350° C.; wherein the melting of the raw materials takes place at a temperature $T_{AU}$ with 1450° C.≤$T_{AU}$≤1600° C.; wherein the used powder of the stabilizer further has a particle size $d_{10}$=0.5·x and/or $d_{90}$=1.5·x, especially $d_{10}$=0.5·x and $d_{90}$=1.5·x, with 0.3 μm≤x≤1.5 μm; wherein the melt has a temperature $T_B$ with 1150° C.≤$T_B$≤$T_{AB}$ when it is filled into the molds; wherein the raw materials and/or the melt made of the raw materials is stored in the crucible at the temperature $T_{AU}$ for the time $t_H$ with $t_H$≥1 h, especially 2 h≤$t_H$≤7 h; wherein the melt in the crucible is homogenized by convection, wherein, if necessary, the melt is cooled in the crucible during the homogenization; wherein the melt is cooled in the discharge region of the crucible to a temperature $T_{AB}$, especially with 1200° C.≤$T_{AB}$≤1300° C.; wherein the stabilizer comprises more than 90 wt-% $ZrO_2$, especially more than 95 wt-% $ZrO_2$, preferably more than 97.5 wt-% $ZrO_2$; wherein after melting and homogenizing the raw materials in the crucible, especially by convection, the melt is immediately poured into the molds; wherein the melt in the crucible is cooled to a temperature $T_M$ with $T_M$≥600° C. with a cooling rate A with 5 K/sec≤A≤100 K/sec; wherein the composition of the blank comprises (data in % by weight):

|  |  |
|---|---|
| $SiO_2$ | 46.0-72.0 |
| $Li_2O$ | 10.0-25.0 |
| $ZrO_2$ | 8.0-20.0 |
| $Al_2O_3$ | 0.1-8.0 |
| $K_2O$ | 0.1-5.0 |
| $CeO_2$ | 0.0-4.0 |
| $B_2O_3$ | 0.0-4.0 |
| $Na_2O$ | 0.0-4.0 |
| $Tb_4O_7$ | 0.0-2.5 | at least one nucleating agent 1.0-10.0, such as $P_2O_5$, and 0.0 to 4.0 of at least one additive, wherein the additive is at least an oxide selected from the group BaO, CaO, MgO, MnO, $Er_2O_3$, $Pr_6O_{11}$, $Sm_2O_3$, $TiO_2$, $V_2O_5$, $Y_2O_3$, and the total sum is 100 wt-%; wherein the composition of the blank comprises (data in % by weight):

|  |  |
|---|---|
| $SiO_2$ | 58-60 |
| $Li_2O$ | 13.5-20.5 |
| $ZrO_2$ | 9.0-12.5 |
| nucleating agent, | 3.0-7.5, particularly $P_2O_5$, |
| $Al_2O_3$ | 0.5-5.0 |
| $K_2O$ | 0.5-3.5 |
| $CeO_2$ | 0.5-2.5 |
| $B_2O_3$ | 0-3 |
| $Na_2O$ | 0-3 |
| $Tb_4O_7$ | 0-1.5, | wherein the total sum is 100 wt-%; wherein the melt is poured into molds and cooled in the molds, being subjected to at least a first heat treatment W1 at a temperature $T_{W1}$ for a period of time $t_{W1}$, with 620° C.≤$T_{W1}$≤800° C., especially 650° C.≤$T_{W1}$≤750° C., and/or 1 min≤$t_{W1}$≤200 min, preferably 10 min≤$t_{W1}$≤60 min; wherein the first heat treatment W1 is carried out in two steps, wherein especially at a first step a temperature $T_{St1}$ with 630° C.≤$T_{St1}$≤690° C., and/or at a second step a temperature $T_{ST2}$ with 720° C.≤$T_{St2}$≤780° C. is adjusted; wherein the lithium silicate glass-ceramic blank is subjected to a second heat treatment W2 at a temperature $T_{W2}$ for a time $t_{w2}$ after the first heat treatment W1, with 800° C.≤$T_{W2}$≤1040° C., preferably 800° C.≤$T_{W2}$≤900° C., and/or 5 min≤$t_{w2}$≤200 min, preferably 5 min≤$t_{w2}$≤30 min; or any combination thereof It should be appreciated that the above referenced aspects and examples are non-limiting as others exist with the present invention, as shown and described herein. For example, any of the above mentioned aspects or features of the invention may be combined to form other unique configurations, as described herein, demonstrated in the drawings, or otherwise

DETAILED DESCRIPTION OF THE INVENTION

One of the objects of the invention is to provide a method for producing a lithium silicate glass blank making sure that the stabilizer does not recrystallize during any subsequent heat treatment, in particular when lithium disilicate exists as main crystalline phase.

Another object is to make sure that the melt to be poured can be shaped on an industrial scale and in a reproducible manner to dental products, such as pressed pellets, or be molded to blocks to be machined by CAD/CAM-processes. When filling the molds, a so called "sloshing" of the melt within the molds shall be prevented as to avoid that the desired smooth, horizontally extending surface of the solidified blanks could not be obtained.

To solve at least one of the above-mentioned problems, the invention provides a method for producing a lithium silicate glass blank with at least 8 wt-%, preferably 9 to 20 wt-%, of a stabilizer selected from the group $ZrO_2$, $HfO_2$, or mixtures thereof comprising the method steps: mixing the raw materials comprising the stabilizer in powder form, wherein the powder of the stabilizer has a particle size $d_{50}$=x with 0.3 μm≤x≤1.5 μm; melting the raw materials in a crucible at a temperature $T_{AU}$ and storing the melt in the crucible for a time $t_H$, pouring the homogenized melt into molds, wherein the melt flows out of the crucible with a discharge temperature $T_{AB}$ being $T_{AU}$≥$T_{AB}$, wherein the filling of the molds and the molding of the melt in the molds takes place with a cooling rate A.

The invention is also characterized by a method for producing a lithium silicate glass blank with a composition of at least 8 wt-%, preferably 9 to 20 wt-%, of a stabilizer selected from the group $ZrO_2$, $HfO_2$, or mixtures thereof, with the method steps: mixing the raw materials comprising the stabilizer in powder form, wherein the powder of the stabilizer has a particle size $d_{50}$=x with 0.3 μm≤x≤1.5 μm, melting the raw materials in a crucible at a temperature $T_{AU}$ and storing the melt in the crucible for a time $t_H$, pouring the homogenized melt into molds, wherein the melt flows out of the crucible with a discharge temperature $T_{AB}$ being $T_{AU}$-Y° C.=$T_{AB}$ with 150° C.≤Y≤350° C. and $T_{AU}$≥1400° C., wherein the filling of the molds and the molding of the melt in the molds takes place with a cooling rate A.

According to the invention, a method for producing a lithium silicate glass blank with a composition of at least 8 wt-%, preferably 9 to 20 wt-%, of a stabilizer selected from the group $ZrO_2$, $HfO_2$, or mixtures thereof, comprises the method steps: mixing the raw materials comprising the stabilizer in powder form, wherein the powder of the stabilizer has a particle size $d_{50}=x$ with 0.3 µm≤x≤1.5 µm, melting the raw materials in a crucible at a temperature $T_{AU}$ and storing the melt in the crucible for a time $t_H$, pouring the homogenized melt into molds, wherein the melt flows out of the crucible with a discharge temperature $T_{AB}$ being $T_{AU} \geq T_{AB}$, wherein the filling of the molds and the molding of the melt in the molds takes place with a cooling rate A with 5 K/sec≤A≤100 K/sec up to a temperature $T_M$ with $T_M \geq 600°$ C., particularly 600° C.≤$T_M$≤650° C.

The invention also relates to a method for producing a lithium silicate glass blank with a composition of at least 8 wt-%, preferably 9 to 20 wt-%, of a stabilizer selected from the group $ZrO_2$, $HfO_2$, or mixtures thereof, wherein the method comprises the steps: mixing the raw materials comprising the stabilizer in powder form, wherein the powder of the stabilizer has a particle size $d_{50}=x$ with 0.3 µm≤x≤1.5 µm, melting the raw materials in a crucible at a temperature $T_{AU}$ with 1450° C.≤$T_{AU}$≤1600° C. and storing the melt in the crucible for a time $t_H$ with $t_H \geq 1$ h, pouring the homogenized melt into molds, wherein the melt flows out of the crucible with a discharge temperature $T_{AB}$ being $T_{AU} \geq T_{AB}$, wherein the filling of the molds and the molding of the melt in the molds takes place with a cooling rate A.

The invention relates in particular to a method for producing a lithium silicate glass blank with a composition with at least 8 wt-%, preferably 9 to 20 wt-%, of a stabilizer selected from the group $ZrO_2$, $HfO_2$, or mixtures thereof, comprising the method steps: mixing the raw materials comprising the stabilizer in powder form, wherein the powder of the stabilizer has a particle size $d_{50}=x$ with 0.3 µm≤x≤1.5 µm, melting the raw materials in a crucible at a temperature $T_{AU}$ with 1450° C.≤$T_{AU}$≤1600° C. and storing the melt in the crucible for a time $t_H$ with $t_H \geq 1$ h, pouring the homogenized melt into molds, wherein the melt flows out of the crucible with a discharge temperature $T_{AB}$ being $T_{AU}-Y°$ C.=$T_{AB}$ with 150° C.≤Y≤350° C. and $T_{AU} \geq 1400°$ C., wherein the filling of the molds and the molding of the melt in the molds takes place with a cooling rate A with 5 K/sec≤A≤100 K/sec up to a temperature $T_M$ with 600° C.≤$T_M$, particularly 600° C.≤$T_M$≤650° C.

It has surprisingly been shown that, when the stabilizer in powder form, especially zirconium oxide powder, has a particle size $d_{50}$ between 0.3 µm and 1.5 µm, the zirconium oxide dissolves well and remains in solution, namely is existent in an amorphous phase, i.e., the glass, even when the melt is poured into the crucible, cooled and then being subjected to one or several heat treatments to form at least lithium disilicate crystals. At the same time, there is the advantage that problems with agglomeration do not occur.

The terms $d_{50}$, $d_{10}$, $d_{90}$ mean that 50%, and 10%, and 90%, respectively, of the particles have a particle size that is smaller than the given value for the particle size.

To avoid "sloshing," it has been proven advantageous when the glass melt flows out of the crucible with a discharge temperature $T_{AB}$ 1200° C.≤$T_{AB}$≤1350° C., preferably 1250° C.≤$T_{AB}$≤1300° C. When the melt is filled into the molds, the melt should have a temperature $T_B$ not less than $T_B=1150°$ C. without any disadvantages being observed as to the finished shape of the lithium silicate glass blanks after the melt has cooled in the crucible.

Cooling the melt in comparison with the temperature used for melting the raw materials and homogenizing them by convection without using mechanical auxiliary means, such as a stirrer, provides the advantage that the melt has a viscosity which makes it possible to fill the molds in a reproducible manner and to obtain a horizontally extending surface at the same time. Possibly, the prevention of recrystallization is also supported by the melt in the crucible cooling with a cooling rate in a range between 5 K/sec and 100 K/sec which prevents the forming of nuclei for the stabilizer material. The cooling rate is applicable at least up to a temperature $T_M \geq 600°$ C., especially 600° C.≤$T_M$≤650° C.

Subsequently, a cooling to room temperature can take place in the usual fashion.

The homogenizing of the melt is also important, wherein it has proved advantageous, when the melt is kept at a temperature $T_{AU}$ which is between 1500° C. and the heat resistance of the used crucible material, such as platinum alloy, for a time of at least 1 hour, especially for a time period between 2 and 7 hours. A multiple melting is not necessary.

Thus, the invention is also characterized in that after melting and homogenizing the raw materials in the crucible, especially by convection, the melt is poured into the molds immediately.

Consequently, the invention, and in its difference over the art, is preferably characterized in that it is not necessary to produce and remelt a frit without causing disadvantages with regard to the homogenization. Thus, in the light of the prior art, the invention provides in general a shorter duration of proceedings and/or a more cost-effective production of the blank.

Of course, the invention is not left if a frit is produced that is remelted.

It is also possible to cool the melt which is homogenized in the crucible by convection during the homogenization process. In doing so, the melt can be kept, for instance, for a first period of time of 2 to 6 hours at a temperature $T_1$ with 1450° C.≤$T_1$≤1550° C., and then kept for a second period of time at a temperature 1200° C.≤$t_2$≤1300° C. for a time $t_2$, to be subsequently poured to fill the molds.

The invention is particularly characterized in that the used powder of the stabilizer further has a particle size $d_{10}=0.5·x$ and/or $d_{90}=1.5·x$, especially $d_{10}=0.5·x$ and $d_{90}=1.59·x$, with 0.3 µm≤x≤1.5 µm.

The aforementioned secondary conditions ensure that the content of small particles is so low that agglomeration does not occur. Limiting the number of large particles also a sufficient dissolution of the stabilizer is ensured.

It is specifically provided that the stabilizer comprises more than 90 wt-% $ZrO_2$, especially more than 95 wt-% $ZrO_2$, preferably more than 97.5 wt-% $ZrO_2$.

Preferably, the composition of the blank comprises the following components (data in % by weight):

| | |
|---|---|
| $SiO_2$ | 46.0-72.0 |
| $Li_2O$ | 10.0-25.0 |
| $ZrO_2$ | 8.0-20.0 |
| $Al_2O_3$ | 0.1-8.0 |
| $K_2O$ | 0.1-5.0 |
| $CeO_2$ | 0.0-4.0 |
| $B_2O_3$ | 0.0-4.0 |
| $Na_2O$ | 0.0-4.0 |
| $Tb_4O_7$ | 0.0-2.5 | at least one nucleating agent 1.0-10.0, such as $P_2O_5$, and 0 to 4.0 of at least one additive,
wherein the total sum is 100 wt-%.

The additive can be at least one oxide selected from the group BaO, CaO, MgO, MnO, $Er_2O_3$, $Pr_6O_{11}$, $SM_2O_3$, $TiO_2$, $V_2O_5$, $Y_2O_3$.

Further, the invention is characterized by a method for producing a lithium silicate glass-ceramic blank by using the lithium silicate glass blank, according to one or more of the aforementioned method steps, wherein the cooled melt which was poured into molds is subjected to at least a first heat treatment W1 at a temperature $T_{W1}$ for a period of time $t_{W1}$ with 620° C.≤$T_{w1}$≤800° C. especially 650° C.≤$T_{w1}$≤750° C., and/or 1 min≤$t_{w1}$≤200 min, preferably 10 min≤$t_{w1}$≤60 min.

By carrying out this step, nucleating agents and lithium metasilicate crystals are formed.

Such a lithium silicate glass-ceramic blank can easily be machined with a minimal wear of tools. Such a blank can also be pressed to a desired geometry.

Particularly to achieve a final crystallization, especially to form lithium disilicate crystals and/or to convert the metasilicate crystals into disilicate crystals, it is provided that the lithium silicate glass-ceramic blank is subjected after the first heat treatment W1 to a second heat treatment W2 at a temperature $T_{w2}$ for a time $t_{w2}$, with 800° C.≤$T_{w2}$≤1040° C., preferably 800° C.≤$T_{w2}$≤900° C., and/or 5 min≤$t_{w2}$≤200 min, preferably 5 min≤$t_{w2}$≤30 min.

For the heat treatment steps leading to nucleation and precrystallization and final crystallization respectively, preferably the following temperature values and heating rates are chosen. Regarding the first heat treatment, it is specifically provided for it to be carried out in two steps, wherein at a first step, the temperature is held between 640° C. and 680° C., and at a second holding step between 720° C. and 780° C. The heated blank is kept at every step for a period of time, wherein at the first step the period of time is between 35 and 45 minutes, and at the second step between 15 and 25 minutes.

Such lithium silicate glass-ceramic blanks show a high translucence and chemical stability. They are characterized by their strength. A precipitation of stabilizer material, especially zirconium oxide, cannot be found. Thus, said lithium silicate glass blanks are especially suitable for dental materials or as components of dental materials, wherein shaped dental products in the form of, for instance, inlays, onlays, bridges, veneers, facets, crowns, partial crowns, abutments can be used.

Especially lithium silicate glass-ceramic blanks are extremely easy to machine by CAD/CAM, wherein after the further heat treatment a high translucent and high-strength product is provided which has a high chemical stability.

Further details, advantages and features of the invention derive not only from the claims and their features, per se and/or in combination, but also from the following examples.

Raw materials, such as lithium carbonate, quartz, aluminum oxide, zirconium oxide were mixed on an industrial scale by means of a tumble mixer until a visually homogeneous mixture existed. In doing so, a total of 5 mixtures were produced, differing from each other in the particle size of the zirconium oxide.

The composition of the test pieces for the conducted tests was the following (data in % by weight):

| | |
|---|---|
| $SiO_2$ | 58-60 |
| $Li_2O$ | 13.5-20.5 |
| $ZrO_2$ | 9.0-12.5 |
| $P_2O_5$ | 3.0-7.5 |
| $Al_2O_3$ | 0.5-6.0 |
| $K_2O$ | 0.5-3.5 |
| $CeO_2$ | 0.5-2.5 |
| $B_2O_3$ | 0-3 |
| $Na_2O$ | 0-3 |
| $Tb_4O_7$ | 0-1.5 |

Example 1

A zirconium oxide powder with a particle size $d_{50}$=approximately 15 μm, $d_{10}$=10.8 μm, $d_{90}$=34.9 μm was used.

The mixture was molten in a high temperature resistant crucible made of platinum alloy at 1450° C. for a time of 2.25 hours. Then, the melt was cooled in the crucible, at first kept at 1450° C. for half an hour, and then kept at 1250° C. for half an hour. Subsequently, the melt was poured into molds suitable for pressed pellets or blocks to be machined. The pellets and blocks respectively should have a volume of 1 $cm^3$ to 2 $cm^3$. The cooling rate was 70 K/sec up to 600° C., then, a cooling down to room temperature took place. An amorphous and, thus, translucent glass was obtained. Then, the blanks were subjected to a crystallization firing, wherein during the first heat treatment the blanks were kept at 660° C. for 60 minutes, and then, during a second heat treatment, kept at 850° C. for 8 minutes. Then a cooling down to room temperature took place. During an inspection of the glass-ceramic, single zirconium oxide precipitations were found which made the glass-ceramic opaque.

Example 2

Zirconium oxide powder with a particle size $d_{50}$=approximately 0.7 μm, $d_{10}$=0.2 μm, $d_{90}$=2.2 μm was used.

The mixture was molten in a high temperature resistant crucible made of platinum alloy for a time T=1500° C. and kept at this temperature for 6 hours. Subsequently, the melt was poured into molds suitable for pressed pellets or blocks to be machined. The pellets and blocks respectively should have a volume of 1 $cm^3$ to 2 $cm^3$. The cooling rate was 70 K/sec up to 600° C. Then, a cooling down to room temperature took place. An amorphous and, thus, translucent glass was obtained. Then, the blanks were subjected to a crystallization firing. For nucleation and/or precrystallization the glass was at first heated with a heating rate of 2 K/min from room temperature to 660° C., and kept at this temperature for 40 minutes. Then a further heating took place to 750° C. with a heating rate of 10 K/min. This temperature was kept for 20 minutes. The final crystallization followed subsequently at a temperature of 850° C. for 8 minutes. Then a cooling down to room temperature took place. During an inspection of the glass-ceramic no zirconium oxide precipitations were found.

Example 3

A zirconium oxide powder with a particle size $d_{50}$=approximately 0.7 μm, $d_{10}$=0.2 μm, $d_{90}$=2.2 μm was used.

The mixture was molten in a high temperature resistant crucible made of platinum alloy at 1500° C. for a time of 6 hours. The melt was then cooled in the crucible and kept at 1250° C. for half an hour. Subsequently, the melt was poured into molds suitable for pressed pellets or blocks to be machined. The pellets and blocks respectively should have a volume of 1 cm³ to 2 cm³. The cooling rate was 70 K/sec up to 600° C. Then, a cooling down to room temperature took place. An amorphous and, thus, translucent glass was obtained. Then the blanks were subjected to a crystallization fire. For nucleation and/or precrystallization the glass was at first heated from room temperature to 660° C. with a heating rate of 2 K/min, and kept at this temperature for 40 minutes. Subsequently, a further heating to 750° C. with a heating rate of 10 K/min took place. This temperature was kept for 20 minutes. Subsequently, the final crystallization took place at a temperature of 850° C. for 8 minutes. Then a cooling down to room temperature took place. During an inspection of the glass-ceramic, no zirconium oxide precipitations were found.

Example 4

A zirconium oxide powder with a particle size $d_{50}$=approximately 0.7 μm, $d_{10}$=0.2 μm, $d_{90}$=2.2 μm was used.

The mixture was molten in a high temperature resistant crucible made of platinum alloy at 1500° C. for a time of 6 hours. The melt was then cooled and kept in the crucible at 1200° C. for half an hour. Subsequently, the melt was poured into molds suitable for pressed pellets or blocks to be machined. The pellets and blocks respectively should have a volume of 1 cm³ to 2 cm³. Then a cooling down to room temperature took place. An amorphous and, thus, translucent glass was obtained. Then the blanks were subjected to a crystallization fire. In doing so, the glass was at first heated from room temperature to 660° C. with a heating rate of 2 K/min, and kept at this temperature for 40 minutes. Subsequently, a further heating to 750° C. with a heating rate of 10 K/min took place. This temperature was kept for 20 minutes. Subsequently, the final crystallization took place at a temperature of 850° C. for 8 minutes. Then a cooling down to room temperature took place. During an inspection of the glass-ceramic single zirconium oxide precipitations were found that made the glass-ceramic opaque.

Example 5

A zirconium oxide powder with a particle size $d_{50}$=approximately 5 μm, $d_{10}$=0.3 μm, $d_{90}$=5.8 μm was used.

The mixture was molten in a high temperature resistant crucible made of platinum alloy at 1500° C. for a time of 4 hours. The melt was then cooled in the crucible and kept at 1450° C. for one hour. Subsequently, the melt was poured into molds suitable for pressed pellets or blocks to be machined. The pellets and blocks should have a volume of 1 cm³ to 2 cm³. The cooling rate was 70 K/sec up to 600° C. Then, a cooling down to room temperature took place. An amorphous and, thus, translucent glass was obtained. Then the blanks were subjected to a crystallization firing, wherein the blanks were kept at 620° C. for 60 minutes (precrystallization), and then, during a second heat treatment, kept at 850° C. for 8 minutes (final crystallization). Then a cooling to room temperature took place. During an inspection of the glass-ceramic, numerous small precipitations of zirconium oxide were found that made the glass-ceramic opaque.

It follows from the aforementioned examples that by using zirconium oxide powder with a particle size of $d_{50}$=0.7 μm, a melting temperature of 1500° C. and a discharge temperature that is lower than the melting temperature, glass-ceramic bodies can be produced in which zirconium precipitations cannot be found. The glass-ceramic bodies had a high translucence. Chemical and mechanical tests showed a high durability and strength.

Each feature disclosed in this specification (including any accompanying claims, abstract, and drawings), may be replaced by alternative features having the same, equivalent or similar purpose, unless expressly stated otherwise. Thus, unless expressly stated otherwise, each feature disclosed is one example only of a generic series of equivalent or similar features.

While preferred embodiments of the present invention have been shown and described herein, it will be obvious to those skilled in the art that such embodiments are provided by way of example only. Numerous variations, changes, and substitutions will be apparent to those skilled in the art without departing from the invention. Other foreseen embodiments or uses for the present invention include the use of the invention in the field of phacoemulsification, where a tip assembly such as the present invention may offer many advantages. Accordingly, it is intended that the invention be limited only by the scope of the appended claims

The invention claimed is:

1. A method for producing a lithium silicate glass blank with a composition of at least 8 wt-% of a stabilizer selected from the group consisting of $ZrO_2$, $HfO_2$, and mixtures thereof, comprising the method steps of:
   mixing the raw materials comprising the stabilizer in powder form, wherein the powder of the stabilizer has a particle size $d_{50}$=x with 0.3 μm≤x≤1.5 μm,
   melting the raw materials in a crucible at a temperature $T_{AU}$ and storing the melt in the crucible for a time $t_H$,
   pouring the homogenized melt into molds, wherein the melt flows out of the crucible with a discharge temperature $T_{AB}$ being $T_{AU} \geq T_{AB}$, wherein the filling of the molds and the molding of the melt in the molds takes place with a cooling rate A.

2. The method according to claim 1, wherein 5 K/sec≤A≤100 K/sec up to a temperature $T_M$ with $T_M \geq 600°$ C.

3. The method according to claim 1, wherein the melt flows out of the crucible with a discharge temperature $T_{AB}$ with $T_{AU}-Y°$ C.=$T_{AB}$ with 150° C.≤Y≤350° C.

4. The method according to claim 3, wherein the melt has a temperature $T_B$ with 1150° C.≤$T_B$<$T_{AB}$ when melt is filled into the molds.

5. The method according to claim 1, wherein the melting of the raw materials takes place at a temperature $T_{AU}$ with 1450° C.≤$T_{AU}$≤1600° C.

6. The method according to claim 1, wherein the powder of the stabilizer has a particle size $d_{10}$=0.5·x, $d_{90}$=1.5·x, or both $d_{10}$=0.5·x and $d_{90}$=1.5·x, with 0.3 μm≤x≤1.5 μm.

7. The method according to claim 1, wherein the melt in the crucible is homogenized by convection and the melt is cooled in the crucible during the homogenization.

8. The method according to claim 1, wherein the melt is cooled in the discharge region of the crucible to a temperature $T_{AB}$ with 1200° C.≤$T_{AB}$≤1300° C.

9. The method according to claim 8, wherein the first heat treatment W1 is carried out in two steps having a first step at a temperature $T_{St1}$ with 630° C.≤$T_{St1}$≤690° C. and a second step at a temperature $T_{ST2}$ with 720° C.≤$T_{St2}$≤780° C.

10. The method according to claim 1, wherein the stabilizer comprises more than 90 wt-% $ZrO_2$.

11. The method according to claim 10, wherein the lithium silicate glass-ceramic blank is subjected to a second heat treatment W2 at a temperature $T_{W2}$ for a time $t_{w2}$ after the first heat treatment W1, with 800° C.$\leq T_{W2}<$1040° C. and 5 min$\leq t_{W2}\leq$200 min.

12. The method according to claim 1, wherein after melting and homogenizing the raw materials in the crucible by convection, the melt is immediately poured into the molds.

13. The method according to claim 1, wherein the melt in the crucible is cooled to a temperature $T_M$ with $T_M \geq$600° C. with a cooling rate A with 5 K/sec$\leq$A$\leq$100 K/sec.

14. The method according to claim 1, wherein the composition of the blank comprises (data in % by weight):

| | |
|---|---|
| $SiO_2$ | 46.0-72.0 |
| $Li_2O$ | 10.0-25.0 |
| $ZrO_2$ | 8.0-20.0 |
| $Al_2O_3$ | 0.1-8.0 |
| $K_2O$ | 0.1-5.0 |
| $CeO_2$ | 0.0-4.0 |
| $B_2O_3$ | 0.0-4.0 |
| $Na_2O$ | 0.0-4.0 |
| $Tb_4O_7$ | 0.0-2.5 | at least one nucleating agent 1.0-10.0, and
0.0 to 4.0 of at least one additive,
wherein the additive is at least an oxide selected from the group consisting of BaO, CaO, MgO, MnO, $Er_2O_3$, $Pr_6O_{11}$, $Sm_2O_3$, $TiO_2$, $V_2O_5$, and $Y_2O_3$, and
the total sum is 100 wt-%.

15. The method according to claim 1, wherein the composition of the blank comprises (data in % by weight):

| | |
|---|---|
| $SiO_2$ | 58-60 |
| $Li_2O$ | 13.5-20.5 |
| $ZrO_2$ | 9.0-12.5 |
| nucleating agent, | 3.0-7.5, particularly P2O5, |
| $Al_2O_3$ | 0.5-6.0 |
| $K_2O$ | 0.5-3.5 |
| $CeO_2$ | 0.5-2.5 |
| $B_2O_3$ | 0-3 |
| $Na_2O$ | 0-3 |
| $Tb_4O_7$ | 0-1.5, | wherein the total sum is 100 wt-%.

16. A method for producing a lithium silicate glass-ceramic blank by using the lithium silicate glass blank according to claim 1, wherein the melt is poured into one or more molds and cooled in the one or more molds, being subjected to at least a first heat treatment W1 at a temperature $T_{W1}$ for a period of time $t_{W1}$, with 620° C.$\leq T_{W1} \leq$800° C. and 1 min$\leq t_{W1}\leq$200 min.

17. The method according to claim 1, wherein the melt has a discharge temperature $T_B$ with 1150° C.$\leq T_B<T_{AB}$ when the melt is filled into the one or more molds.

18. The method according to claim 1, wherein the raw materials and/or the melt is made of the raw materials stored in the crucible at the temperature $T_{AU}$ for the time $t_H$ with $t_H \geq$1 h.

19. A dental product made of a lithium silicate glass-ceramic blank according claim 8.

20. A method for producing a lithium silicate glass blank with a composition of at least 8 wt-% of a stabilizer selected from the group consisting of $ZrO_2$, $HfO_2$, and mixtures thereof, comprising the method steps of:
mixing the raw materials comprising the stabilizer in powder form, wherein the powder of the stabilizer has a particle size $d_{50}=x$ with 0.3 µm$\leq$x$\leq$1.5 µm,
melting the raw materials in a crucible at a temperature $T_{AU}$ and storing the melt in the crucible for a time $t_H$,
pouring the homogenized melt into one or more molds, wherein the melt flows out of the crucible with a discharge temperature $T_{AB}$ being $T_{AU}-Y°$ C.$=T_{AB}$ with 150° C.$\leq$Y$\leq$350° C. and $T_{AU}\geq$1400° C., wherein the filling of the one or more molds and the shaping of the melt in the molds takes place with a cooling rate A.

21. The method according to claim 20, wherein the melt flows out of the crucible with a discharge temperature $T_{AB}$ with $T_{AU}-Y°$ C.$=T_{AB}$ with 150° C.$\leq$Y$\leq$350° C.

22. The method according to claim 21, wherein the melt has a discharge temperature $T_B$ with 1150° C.$\leq T_B<T_{AB}$ when the melt is filled into the one or more molds.

23. The method according to claim 20, wherein the melting of the raw materials takes place at a temperature $T_{AU}$ with 1450° C.$\leq T_{AU}\leq$1600° C.

24. The method according to claim 20, wherein the used powder of the stabilizer further has a particle size $d_{10}$=0.5·x, $d_{90}$=1.5·x, or both $d_{10}$=0.5·x and $d_{90}$=1.5·x, with 0.3 µm$\leq$x$\leq$1.5 µm.

25. The method according to claim 20, wherein 1450° C.$\leq T_{AU}\leq$1600° C. and storing the melt in the crucible for a time $t_H$ with $t_H\geq$1 h.

26. A method for producing lithium silicate glass blank with a composition of at least 8 wt-% of a stabilizer selected from the group consisting of $ZrO_2$, $HfO_2$, and mixtures thereof, comprising the method steps of:
mixing the raw materials comprising the stabilizer in powder form, wherein the powder of the stabilizer has a particle size $d_{50}=x$ with 0.3 µm$\leq$x$\leq$1.5 µm,
melting the raw materials in a crucible at a temperature $T_{AU}$ with 1450° C.$\leq T_{AU}\leq$1600° C. and storing the melt in the crucible for a time $t_H$ with $t_H\geq$1 h,
pouring the homogenized melt into one or more molds, wherein the melt flows out of the crucible with a discharge temperature $T_{AB}$ being $T_{AU}-Y°$ C.$=T_{AB}$ with 150° C.$\leq$Y$\leq$350° C. and $T_{AU}\geq$1400° C., wherein the filling of the one or more molds and the molding of the melt in the one or more molds takes place with a cooling rate A with 5 K/sec$\leq$A$\leq$100 K/sec up to a temperature $T_M$ with 600° C.$\geq T_M$.

27. The method according to claim 26, wherein the melt flows out of the crucible with a discharge temperature $T_{AB}$ with $T_{AU}-Y°$ C.$=T_{AB}$ with 150° C.$\leq$Y$\leq$350° C.

28. The method according to claim 26, wherein the melting of the raw materials takes place at a temperature $T_{AU}$ with 1450° C.$\leq T_{AU}\leq$1600° C.

29. The method according to claim 26, wherein the powder of the stabilizer has a particle size $d_{10}$=0.5·x, $d_{90}$=1.5·x, or both $d_{10}$=0.5·x and $d_{90}$=1.5·x, with 0.3 µm$\leq$x$\leq$1.5 µm.

* * * * *